(12) United States Patent
Naef et al.

(10) Patent No.: US 7,345,206 B2
(45) Date of Patent: Mar. 18, 2008

(54) PROCESS FOR THE DIMERISATION OF ALKYL GLYOXALS

(75) Inventors: Ferdinand Naef, Seewen (CH); René Decorzant, Onex (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/692,809

(22) Filed: Mar. 28, 2007

(65) Prior Publication Data

US 2007/0185352 A1 Aug. 9, 2007

Related U.S. Application Data

(63) Continuation of application No. PCT/IB2005/053489, filed on Oct. 25, 2005.

(30) Foreign Application Priority Data

Nov. 2, 2004 (WO) ................. PCT/IB2004/003636

(51) Int. Cl.
  *C07C 45/45* (2006.01)
(52) U.S. Cl. ...................... 568/388; 568/397
(58) Field of Classification Search .................... None
  See application file for complete search history.

(56) References Cited

U.S. PATENT DOCUMENTS 3,558,714 A 1/1971 Buchi .......................... 260/594

FOREIGN PATENT DOCUMENTS

EP 0 368 211 B1 8/1992

OTHER PUBLICATIONS

George Buchi et al., "Syntheses of 2,5-Dimethyl-4-hydroxy-2,3-dihydrofuran-3-one (Furaneol), a Flavor Principle of Pineapple and Strawberry", J. Org, Chem., vol. 38, No. 1, pp. 123-125 (1978).
Luciano Bassignani et al., "Novel Applications of the Potassium Chlorate Osmium Tetroxide Oxidizing System. Synthesis of α-Diearbonyl Derivatives from Acetylenic Compounds. Synthesis of a 2,3-Dihydroxy-1,4-dione from a 2,5-Dialkylfuran", J. Org, Chem., vol. 43, No. 21, pp. 4245-4247 (1978).
Angelo Clerici et al., "Radical Addition to the Carbonyl Carbon Promoted by Aqueous Titanium Trichloride: Stereoselective Synthesis of α,β,8-Dihydroxy Ketones", , J. Org, Chem., vol. 54, No. 16, pp. 3872-3882 (1978).
Glen A. Russell et al., "β-Keto Sulfoxides. II. Transformations Giving Sulfur-Free Products", Journal of the American Chemical Society, vol. 88, No. 23, pp. 5498-5504 (1966).
Mark A. Briggs et al., "Synthesis of 4-Hydroxy-2,5-dimethylfuran-3(2H)-one (Furaneol) from (2R,3R)—tartaric Acid", Journal of Chem. Soc. Perkin Trans. 1, pp. 795-798 (1985).
Reynold C. Fuson et al. XP001021797, "1,2-Ciacylethylene Glycols", vol. 61, pp. 3246-3249 (1939).

*Primary Examiner*—Sikarl A. Witherspoon
(74) *Attorney, Agent, or Firm*—Winston & Strawn LLP

(57) ABSTRACT

The present invention relates to the field of organic synthesis and more particularly to a new process for the dimerisation of alkyl glyoxals, said process being promoted by an alkaline salt of the hydroxymethanesulfinic acid and is performed at a pH comprised between 3.5 and 9.5.

11 Claims, No Drawings

PROCESS FOR THE DIMERISATION OF ALKYL GLYOXALS

CROSS-REFERENCE TO RELATED APPLICATIONS

This application is a continuation of International application PCT/IB2005/053489 filed Oct. 25, 2005, the entire content of which is expressly incorporated herein by reference thereto.

TECHNICAL FIELD

The present invention relates to the field of organic synthesis and more particularly to a new process for the preparation of 1,4-dione-2,3-diols as defined further below.

BACKGROUND

Various processes for the preparation of compounds of formula (I) have been reported, for example Briggs et al, J. Chem. Soc. Perkin. Trans. I, 1985, 795 relates to a multistep synthesis of the 3,4-dihydroxyhexane-2,5-dione starting from the tartaric acid, or Bassignani et al, J. Org. Chem., 1978, 43, 4245 relates to the synthesis of the 3,4-dihydroxyhexane-2,5-dione by oxidizing the expensive 2,5-dimethylfuran with the toxic and expensive $KClO_3/OsO_4$ system.

Another reported method to synthesise compounds (I) is the reductive dimerisation of glyoxals. However, despite the fact that this reaction allows to obtain compound (I) as the final product in only one step and from easily available glyoxals (II), said reaction has attracted only little attention.

To our knowledge, the prior art discloses only four different processes to dimerise glyoxals:

a) European patent EP 368211 B1 discloses an electrochemical process to dimerise alkyl glyoxals with a yield of about 47%.
b) Büchi et al, J. Org. Chem., 1973, 38, 123 teach the use of metallic Zn to promote the dimerisation of methyl glyoxal with a yield of about 55%.
c) Clerici et al, J. Org. Chem., 1989, 54, 3872 teach the use of $TiCl_3$ to promote the dimerisation of phenylglyoxal with a yield of about 30%.
d) Russell et al, J. Am. Chem. Soc., 1966, 88, 5498 teach the use of Cu(I), obtained in situ from $Cu(NO_3)_2$ and $HOCH_2SO_2Na.2H_2O$, to promote the dimerisation of phenylglyoxal with a yield of about 60-70%.

The methods mentioned hereinabove suffer of their low yield (generally lower than 70%) and/or of the use of at least 0.1 equivalent of heavy metal salt which implies problems of purification of the final product and of waste treatment. Therefore there is still a need to find a process to achieve the reductive dimerisation of glyoxals with high yield and without using heavy metals as coreactants.

SUMMARY OF THE INVENTION

The present invention now relates to the preparation of compounds of formula (I) by the reductive dimerisation of an alkyl glyoxal (II) promoted by an alkaline salt of the hydroxymethanesulfinic acid ($HOCH_2SO_2M$), preferably $HOCH_2SO_2Na.2H_2O$, according to Scheme (1):

Scheme 1: Reductive Dimerisation of Glyoxals According to the Invention

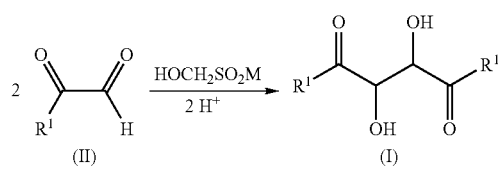

wherein $R^1$ represents simultaneously a linear or branched $C_1$ to $C_5$ alkyl group, and M is an alkaline metal ion.

DETAILED DESCRIPTION OF THE PREFERRED EMBODIMENTS

In order to overcome the problems aforementioned, the present invention relates to a new process aimed at the synthesis of compounds (I) in a single step and with high yields.

The process of the invention concerns more specifically the dimerisation of glyoxals (II). Indeed, we have now surprisingly discovered that an alkaline salt of the hydroxymethanesulfinic acid, in the presence of a specific pH conditions, is able to promote the reductive dimerisation of glyoxals (II).

Therefore, the process of the invention concerns the preparation of a compound of formula

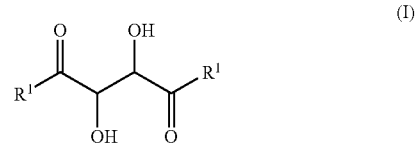

wherein $R^1$ represents a linear or branched $C_1$ to $C_5$ alkyl group, comprising the dimerisation, in a water-based reaction medium, of a glyoxal of formula

wherein $R^1$ has the same meaning as defined above, said process being characterized in that the dimerisation is carried out
a) in the presence of alkaline salt of the hydroxymethanesulfinic acid (i.e. a compound of formula $HOCH_2SO_2M$, M being an alkaline metal ion); and
b) in that the pH of the reaction medium is comprised between 3.5 and 9.5.

According to a particular embodiment of the invention, the starting glyoxal (II) is methyl glyoxal, which provides the preferred final dihydroxy-dione (I), namely the 3,4-dihydroxy-hexane-2,5-dione.

The preferred alkaline salt of the hydroxymethanesulfinic acid is $HOCH_2SO_2Na.2H_2O$, also known as RONGALIT® (origin: BASF, Germany).

Said salt of the hydroxymethanesulfinic acid can be used in the invention's process in the form of a chemical previously prepared and isolated or can be prepared in situ in the reaction medium, without isolation or purification, just before their use. The experimental procedure for its preparation is substantially similar in both cases and is well known by a person skilled in the art. The use of a salt of the hydroxymethanesulfinic in the form of a pre-isolated compound represents a preferred embodiment.

As mentioned above, the dimerisation is carried out in a water-based reaction medium. By "water-based reaction medium" it is meant here the medium wherein the reaction takes place, said medium containing at least 50% of water, percentage being relative to its own weight. According to an embodiment of the invention, a particularly suitable water-based reaction medium is water.

As the process of the invention takes place in a water-based reaction medium and, as shown in Scheme 1, the reduction of glyoxal requires protons, the pH of the solution has great importance for the course of the reaction. In that respect, we have discovered that, in order to ensure high yields of compound (I), it is important to perform the invention's process in a weakly acidic to moderately basic medium. Indeed, if the reaction is performed in a too acid or too basic medium, then the reaction yield is lower.

According to an embodiment of the invention the present process is preferably carried out in a reaction medium having a pH comprised between 4 and 9.5, preferably between 5 and 9, more preferably between 5 and 7.5.

We have also established that the process is advantageously performed in a water-based reaction medium containing a buffering salt, so as to ensure a minimal variation in the concentration of the free protons. The amount of buffering salt used depends on the desired range of pH.

Said buffering salts are derivatives of weak bases or weak acids, and according to an embodiment of the invention they are selected from the group consisting of the alkaline or alkaline-earth carbonates, the alkaline bicarbonates or the mono alkaline phosphates. More preferably the buffering salt is selected from the group consisting of $Na_2CO_3$, $CaCO_3$ and $NaHCO_3$.

According to the stoechiometry of the reaction, the molar ratio Glyoxal (II)/($HOCH_2SO_2M$) is equal to 2. However we have discovered that an excess of $HOCH_2SO_2M$ increases the yield of the process. Therefore, according to an embodiment of the invention, a molar ratio Glyoxal (II)/($HOCH_2SO_2M$) ranging between 2 and 0.3, or between 1.5 and 0.5, can be used advantageously.

The temperature at which the process of the invention can be carried out is comprised between 0° C. and 100° C., more preferably between 20° C. and 60° C.

EXAMPLES

The invention will now be described in further detail by way of the following examples, wherein the temperatures are indicated in degrees centigrade and the abbreviations have the usual meaning in the art.

Example 1

RONGALIT®, calcium carbonate and methyl glyoxal (techn. ~40% in water) are all commercially available from FLUKA (Switzerland).

Dimerisation of Methyl Glyoxal

A 1.5 l glass reactor equipped with mechanical stirring, an argon blanket, a thermometer and a pH-meter, was charged with a 40% aqueous solution of methyl glyoxal (180 g; 1 mole) and water (300 ml). This solution was stirred at 40° and solid sodium carbonate (10 g) was added, the pH rose from 2.6 to 5.5. A solution of RONGALIT® (154 g; 1 mole) in water (500 ml) was added in 15 minutes while the temperature was maintained at 40-43°. The reaction was slightly exothermic, and the pH rose from 5.5 to 7.3 during the introduction and then dropped to 6.3 during the next hour. The reaction was stirred 6 more hours at 40°. It was acidified at 20° to pH 5.0 by addition of 85% phosphoric acid. The water of the reaction mixture was distilled off by vacuum distillation and the residue was extracted three times with 600 ml of ethyl acetate. The combined organic phases were mixed and the solvent was distilled off by vacuum distillation. A bulb to bulb distillation of the crude product, at 0.1 mbar/130-150°, gave 3,4-dihydroxy-hexane-2,5-dione (having the same $^1$H-NMR spectra as those described in Büchi et al, J. Org. Chem., 1973, 38, 123), in 72% of yield.

Example 2

Various experimental conditions have been used, following the same protocol as in Example 1, but adapting the quantities and volumes according to Table 1:

TABLE 1

| | Various experimental conditions | | | | | | |
|---|---|---|---|---|---|---|---|
| Test | Methyl glyoxal | RONGALIT ® | Base | pH range[2] | T (° C.) | Time | Yield |
| 1 | 1 mole | 0.8 mole | $CaCO_3$ 10 g | 5.5/7.3 | 40-43° | 6 h | 70% |
| 2 | 1 mole | 1.1 mole | $CaCO_3$ 10 g | 5.5/7.3 | 40-43° | 6 h | 70% |
| 3 | 0.2 mole | 0.16 mole | $CaCO_3$ 12 g | 5.2/6.8 | 5-20° | 20 h | 75% |
| 4 | 0.25 mole | 0.25 mole | $NaHCO_3$ 10 g | 7.2/8.9 | 0-20° | 8 h | 47% |
| 5 | 0.20 mole | 0.16 mole | $NaHCO_3$ 15 g | 5.5/8.8 | 40° | 6 h | 67% |
| 6 | 1 mole | 0.8 mole | $Na_2CO_3$ 15 g | 7.2/9.3 | 0-20° | 20 h | 50% |
| 7[1] | 0.2 mole | 0.16 mole | — | 2.5/4.0 | 0-20° | 20 h | 31%* |
| 8[1] | 0.2 mole | 0.16 mole | $CaCl_2$ | 1.8/8.0 | 40° | 6 h | 23% |

TABLE 1-continued

Various experimental conditions

| Test | Methyl glyoxal | RONGAL IT ® | Base | pH range[2] | T (° C.) | Time | Yield |
|---|---|---|---|---|---|---|---|
| 9[1] | 0.2 mole | 0.16 mole | Na$_2$CO$_3$ 105 g | 10/10.5 | 0-20° | 20 h | 14% |

[1]process carried out in under conditions not included in that of the invention.
[2]variation of the pH of the reaction medium during the dimerisation.
*= crude yield (no distillation)

Example 3

To sodium dithionite (110 mmoles) dissolved into 50 ml of water (measured pH=6.5) was added a solution of NaOH (120 mmoles) in 25 ml of water and the resulting suspension was stirred for 15 minutes. To this suspension were added 9.5 g (110 mmoles) of formaldahyde (35% in water) and the mixture was stirred for 2 hours at room temperature (pH of the final solution was 9.5). Then 80 ml of ethanol were added and the precipitate filtered off (sodium sulphite). The liquors, containing HOCH$_2$SO$_2$Na, were then added in 15 minutes to 30 ml of water containing 1.8 g (100 mmoles) of methyl glyoxal (40% in water) and 1 g of sodium carbonate (pH=7). The resulting mixture was stirred during 6 hours at room temperature and had a pH varying between 8.2 and 7.7. Acidification with phosphoric acid and work-up as described in Example 1 resulted in the desired compound of formula (I) with a yield of about 55%.

What is claimed is:

1. A process for the preparation of a compound of formula

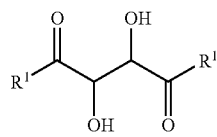

(I)

wherein R$^1$ represents a linear or branched C$_1$ to C$_5$ alkyl group, comprising the dimerisation, in a water-based reaction medium, of a glyoxal of formula

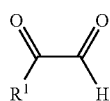

(II)

wherein R$^1$ has the same meaning as defined above, and said dimerisation is carried out a) in the presence of an alkaline salt of hydroxymethanesulfinic acid; and b) in that the pH of the reaction medium is comprised between 3.5 and 9.5, and wherein no heavy metals are present as co-reactants.

2. The process according to claim 1, wherein the compound of formula (II) is methyl glyoxal and the compound of formula (I) is 3,4-dihydroxyhexane-2,5-dione.

3. The process according to claim 1, wherein the alkaline salt of the hydroxymethanesulfinic acid is HOCH$_2$SO$_2$Na.2H$_2$O.

4. The process according to claim 1, wherein the pH is between 4 and 9.5.

5. The process according to claim 4, wherein the pH is between 5 and 9.

6. The process according to claim 4, wherein the pH is between 5 and 7.5.

7. The process according to claim 1, which is carried out in a water-based reaction medium containing a buffering salt.

8. The process according to claim 7, wherein the buffering salt is selected from the group consisting of the alkaline or alkaline-earth carbonates, the alkaline bicarbonates and the mono alkaline phosphates.

9. The process according to claim 7, wherein the buffering salt is selected from the group consisting of Na$_2$CO$_3$, CaCO$_3$ and NaHCO$_3$.

10. The process according to claim 1, carried out at a temperature of between 20° C. and 60° C.

11. The process according to claim 1 wherein the dimerisation is promoted solely by the alkaline salt of the hydroxymethanesulfinic acid.

* * * * *